United States Patent [19]
Huser et al.

[11] Patent Number: 5,488,129
[45] Date of Patent: Jan. 30, 1996

[54] HYDROCYANATION OF OLEFINICALLY UNSATURATED NITRILES INTO DINITRILE COMPOUNDS

[75] Inventors: Marc Huser, Villeurbanne; Robert Perron, Charly, both of France

[73] Assignee: Rhone-Poulenc Chimie, Courbevoie Cedex, France

[21] Appl. No.: 335,349

[22] Filed: Nov. 3, 1994

[30] Foreign Application Priority Data

Nov. 3, 1993 [FR] France .................................. 93 13306

[51] Int. Cl.$^6$ .............................................. C07C 253/10
[52] U.S. Cl. ................................... 558/338; 558/355
[58] Field of Search ................................. 558/338

[56] References Cited

U.S. PATENT DOCUMENTS

| | | | |
|---|---|---|---|
| 3,496,217 | 2/1970 | Drinkard et al. | 558/334 |
| 3,903,120 | 9/1975 | Shook, Jr. et al. | 558/338 X |
| 3,925,445 | 12/1975 | King et al. | 558/338 |
| 4,087,452 | 5/1978 | Kuntz | 558/338 |
| 4,215,068 | 7/1980 | Wu et al. | 558/338 |
| 4,385,007 | 5/1983 | Shook, Jr. | 558/338 |
| 4,705,881 | 11/1987 | Rapoport | 558/334 |
| 4,810,815 | 3/1989 | Bryndza | 558/338 |
| 4,874,884 | 10/1989 | McKinney et al. | 558/338 |
| 5,087,722 | 2/1992 | Inomata et al. | 558/338 |
| 5,087,723 | 2/1992 | McKinney | 558/338 |
| 5,143,873 | 9/1992 | Bryndza et al. | 558/338 X |
| 5,169,971 | 12/1992 | Inomata et al. | 558/338 |

FOREIGN PATENT DOCUMENTS 2338253  8/1977  France .

OTHER PUBLICATIONS

Moore, et al., "Chemistry", (1978), p. 383, McGraw-Hill Book Co., N.Y.

Primary Examiner—Joseph Paul Brust
Attorney, Agent, or Firm—Burns, Doane, Swecker & Mathis

[57] ABSTRACT

Ethylenically unsaturated aliphatic nitriles, for example the linear pentenenitriles, are converted/hydrocyanated into their corresponding dinitriles, for example adiponitrile, by reacting such nitriles with hydrogen cyanide, in an aqueous reaction medium which comprises (1) a catalytically effective amount of a transition metal compound and a sulfonated phosphine, together with (2) a cocatalytically effective amount of at least one Lewis acid; the Lewis acid cocatalyst promotes the linearity of the final product dinitriles and/or prolongs the useful life of the catalyst.

28 Claims, No Drawings

HYDROCYANATION OF OLEFINICALLY UNSATURATED NITRILES INTO DINITRILE COMPOUNDS

BACKGROUND OF THE INVENTION

1. Field of the Invention

The present invention relates to the catalytic hydrocyanation of ethylenically unsaturated nitriles into saturated dinitriles, and, more especially, to the catalytic hydrocyanation of pentenenitriles into adiponitrile, one of the basic starting materials for the production of polyamide or nylon 66.

2. Description of the Prior Art

French Patent No. 1,599,761 describes a process for the preparation of nitriles by addition of hydrocyanic acid to organic compounds containing at least one ethylenic double bond, in the presence of a nickel catalyst and a triaryl phosphite. This reaction may be carried out in the presence or absence of a solvent.

When a solvent is used in this prior art process, it is preferably a hydrocarbon such as benzene or xylenes, or a nitrile such as acetonitrile.

The catalyst is an organonickel complex containing ligands such as phosphines, arsines, stilbenes, phosphites, arsenites or antimonites.

The presence of a promoter to activate the catalyst, such as a boron compound or a metal salt, generally a Lewis acid, is also described in this '761 patent.

In this particular process, the reaction medium is completely organic and a principal disadvantage thereof is the difficulty of separating, at the end of the reaction, the hydrocyanation products from the catalytic solution containing a plurality of constituents (nickel complex, triaryl phosphite, promoter), with a view, in particular, to recycling the catalyst solution to a fresh hydrocyanation reaction. Such a separation is difficult and imperfect, and a substantial loss of catalyst occurs. In addition, the catalyst is present in the products of hydrocyanation.

FR-A-2,338,253 describes the hydrocyanation of compounds having at least one site of ethylenic unsaturation in the presence of an aqueous solution of a compound of a transition metal, in particular nickel, palladium or iron, and a sulfonated phosphine.

This process permits good hydrocyanation, in particular of pentenenitriles, and an easy separation from the catalytic solution by simple decantation.

The results obtained during this latter hydrocyanation reaction are relatively good with various substrates and in particular with functional olefins such as pentenenitriles. Nonetheless, the percentage of linear dinitrile compound formed relative to the totality of the isomers obtained generally does not exceed 65% to 70%.

Furthermore, the catalyst rapidly becomes deactivated.

SUMMARY OF THE INVENTION

Accordingly, a major object of the present invention is the provision of an improved catalytic process for the hydrocyanation of unsaturated nitriles, whereby the degree of linearity of the final products is increased and/or the useful life of the catalyst is prolonged.

Briefly, the present invention features the hydrocyanation of ethylenically unsaturated aliphatic nitriles, comprising reacting same with hydrogen cyanide in the presence of an aqueous solution of a catalyst which comprises a transition metal compound and a sulfonated phosphine, said catalyst solution also comprising at least one Lewis acid cocatalyst.

DETAILED DESCRIPTION OF BEST MODE AND PREFERRED EMBODIMENTS OF THE INVENTION

More particularly according to the present invention, the ethylenically unsaturated nitrile starting materials, advantageously, are linear pentenenitriles such as 3-pentenenitrile, 4-pentenenitrile, and mixtures thereof.

These pentenenitriles may contain amounts, generally minor, of other compounds such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, obtained from a previous hydrocyanation of butadiene and/or from the isomerization of 2-methyl-3-butenenitrile to pentenenitriles.

Compounds of nickel, of palladium and of iron are the preferred transition metal compounds. Compounds which are water-soluble or which dissolve under the conditions of reaction are used. The residue or moiety bonded to or associated with the metal is not critical, as long as it satisfies these conditions.

Among the aforesaid compounds, those most preferred are nickel compounds, exemplary of which are:

(a) compounds in which the nickel is in oxidation state zero, for example potassium tetracyanonickelate $K_4(NiCN_4)$, bis(acrylonitrile)nickel zero, bis(1,5-cyclooctadiene)nickel and derivatives thereof containing ligands of Group Va of the Periodic Table, such as tetrakis(triphenylphosphine)nickel zero (in the latter case the compound may be dissolved in a water-immiscible solvent such as toluene; an aqueous solution of sulfonated phosphine can be used to extract some of the nickel therefrom, and a red color develops in the aqueous solution which separates out by settling);

(b) nickel compounds such as carboxylates (in particular acetate), carbonate, bicarbonate, borate, bromide, chloride, citrate, thiocyanate, cyanide, formate, hydroxide, hydrophosphite, phosphite, phosphate and derivatives thereof, iodide, nitrate, sulfate, sulfite, arylsulfonates and alkylsulfonates.

It is not necessary for the nickel compound itself to be water-soluble. For example, nickel cyanide, which is sparingly soluble in water, is very soluble in an aqueous solution of phosphine.

When the nickel compound used manifests a nickel oxidation state greater than 0, a nickel-reducing agent which preferentially reacts with nickel under the reaction conditions is added to the reaction medium. This reducing agent may be organic or inorganic. Exemplary thereof are $NaBH_4$, Zn powder, magnesium, $KBH_4$ and borohydrides which are preferably water-soluble.

This reducing agent is added in an amount such that the number of redox equivalents ranges from 1 to 10. However, values of less than 1 and greater than 10 are also within the scope of this invention.

When the nickel compound used reflects a nickel oxidation state of 0, it is also possible to add a reducing agent of the type of those indicated above, but this addition is not essential.

When an iron compound is used, the same reducing agents are suitable.

In the case of palladium, the reducing agents may additionally be components of the reaction medium (phosphine, solvent, olefin).

The sulfonated phosphines used in the present process are preferably sulfonated phosphines of general formula (I):

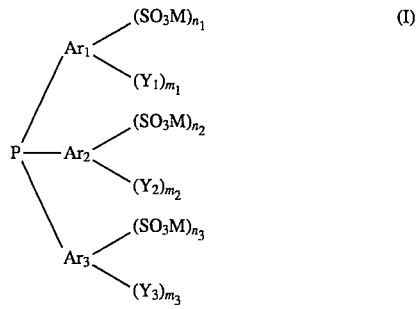

in which $Ar_1$, $Ar_2$ and $Ar_3$, which may be identical or different, are each aryl radicals preferably having from 6 to 10 carbon atoms; $Y_1$, $Y_2$ and $Y_3$, which may be identical or different, are each an alkyl radical having from 1 to 4 carbon atoms, an alkoxy radical having from 1 to 4 carbon atoms, a halogen atom, a CN group, an $NO_2$ group, an OH group, or a radial $NR_1R_2$ wherein $R_1$ and $R_2$, which may be identical or different, are each an alkyl radical having from 1 to 4 carbon atoms; M is an inorganic or organic cationic residue or moiety selected such that the compound-of formula (I) is water-soluble, advantageously from among $H^+$, alkali metal or alkaline earth metal cations, a radical $N(R_3R_4R_5R_6)^+$ wherein $R_3$, $R_4$, $R_5$ and $R_6$, which may be identical or different, are each an alkyl radical having from 1 to 4 carbon atoms or a hydrogen atom, or a cation derived from metals, the benzenesulfonic acid salts of which being water-soluble; $m_1$, $m_2$ and $m_3$ are integers, which may be identical or different, ranging from 0 to 5; and $n_1$, $n_2$ and $n_3$ are integers, which may be identical or different, ranging from 0 to 3, at least one of these being greater than or equal to 1.

Lead, zinc and tin are exemplary metals, the benzenesulfonic acid salts of which are water-soluble.

By the expression "water-soluble" compound is intended a compound having solubility of at least 0.01 g per liter of water.

Among the phosphines of formula (I), those preferred are the compounds in which:

$Ar_1$, $Ar_2$ and $Ar_3$ are phenyl radicals;

$Y_1$, $Y_2$ and $Y_3$ are alkyl radicals having from 1 to 2 carbon atoms, or alkoxy radicals having from 1 to 2 carbon atoms;

M is a cation selected from among $H^+$, cations of Na, K, Ca and Ba, $NH_4^+$, tetramethylammonium, tetraethylammonium, tetrapropylammonium and tetrabutylammonium cations;

$m_1$, $m_2$ and $m_3$ are integers ranging from 0 to 3; and $n_1$, $n_2$ and $n_3$ are integers ranging from 0 to 3, at least one of which being greater than 1.

Among these phosphines, particularly preferred are the sodium, potassium, calcium, barium, ammonium, tetramethylammonium and tetraethylammonium salts of mono(sulfophenyl)diphenylphosphine, di(sulfophenyl)phenylphosphine and tri(sulfophenyl)phosphine, the $SO_3$ groups of which preferably being in the meta-position.

Also exemplary of the phosphines of formula (I) are the alkali metal or alkaline earth metal salts, ammonium salts, and quaternary ammonium salts of (3-sulfo-4-methylphenyl)di(4-methylphenyl)phosphine; of (3-sulfo-4-methoxyphenyl)di(4-methoxyphenyl)phosphine; of (3-sulfo-4-chlorophenyl)di(4-chlorophenyl)phosphine; of di(3-sulfophenyl)phenylphosphine; of di(4-sulfophenyl)phenylphosphine; of di(3-sulfo-4-methylphenyl)(4-methylphenyl)phosphine; of di(3-sulfo-4-methoxyphenyl)(4-methoxyphenyl)phosphine; of di(3-sulfo-4-chlorophenyl)(4-chlorophenyl)phosphine; of tri(3-sulfophenyl)phosphine; of tri(4-sulfophenyl)phosphine; of tri(3-sulfo-4-methylphenyl)phosphine; of tri(3-sulfo-4-methoxyphenyl)phosphine; of tri(3-sulfo-4-chlorophenyl)phosphine; of (2-sulfo-4-methylphenyl)(3-sulfo-4-methylphenyl)(3,5-disulfo-4 methylphenyl)phosphine; and of (3-sulfophenyl)(3-sulfo-4-chlorophenyl)(3,5-disulfo-4-chlorophenyl)phosphine.

It is, of course, also possible to employ a mixture of these phosphines. In particular, a mixture of mono-, di- and tri-meta-sulfonated phosphines may be used.

The sulfonated phosphines employed in the process of the present invention may be prepared according to any one of a number of known processes. Thus, as described in H. Schindlbauer, *Monatsch. Chem.*, 96, pages 2051–2057 (1965), the sodium salt of (p-sulfophenyl)diphenylphosphine may be prepared by reacting sodium p-chlorobenzenesulfonate with diphenylchlorophosphine, in the presence of sodium or potassium. As described in *J. Chem. Soc.*, pages 276–288 (1958) and in GB-1,066,261, phenylphosphines of formula (I) may be prepared via the sulfonation of aromatic ring compounds using oleum, followed by neutralization of the sulfonic groups formed by means of a suitable basic derivative of one of the metals represented by M in the formula (I). The crude sulfonated phosphine obtained may contain, in admixture, the corresponding sulfonated phosphine oxide, the presence of which does not, however, interfere with the hydrocyanation process according to the present invention.

The hydrocyanation reaction is typically carried out at a temperature of 10° C. to 150° C. and preferably of 30° C. to 120° C.

The amount of nickel compound used is selected such that there is from $10^{-4}$ to 1 and preferably from 0.005 to 0.5 mol of nickel per liter of reaction solution.

The amount of phosphine of formula (I) used to prepare the reaction solution is selected such that the number of moles of this compound relative to 1 mol of elemental metal ranges from 0.5 to 2,000 and preferably from 2 to 300.

The Lewis acid cocatalyst improves or enhances the linearity of the final product dinitriles, namely, the percentage of linear dinitrile relative to the totality of the dinitriles formed, and/or prolongs the useful life of the catalyst.

By "Lewis acid" is intended the art-recognized usual definition, namely, compounds which are electron-pair acceptors.

The Lewis acids described in the text edited by G. A. Olah, *Friedel-Crafts and Related Reactions*, volume I, pages 191 to 197 (1963) are particularly representative.

The Lewis acids used as cocatalysts in the subject process are advantageously selected from among compounds of the elements of Groups Ib, IIb, IIIa, IIIb, IVa, IVb, Va, Vb, VIb, VIIb and VIII of the Periodic Table, insofar as said compounds are at least partially soluble and stable in water, or, more generally, in the aqueous phase of the reaction mixture. These compounds are typically salts, in particular halides, preferably chlorides and bromides, sulfates, nitrates, sulfonates, in particular trifluoromethanesulfonates, carboxylates, acetylacetonates, tetrafluoroborates and phosphates.

Exemplary such Lewis acids include zinc chloride, zinc bromide, zinc iodide, zinc trifluoromethanesulfonate, zinc acetate, zinc nitrate, zinc tetrafluoroborate, manganese chloride, manganese bromide, nickel chloride, nickel bromide, nickel cyanide, nickel acetylacetonate, cadmium chloride, cadmium bromide, stannous chloride, stannous bromide, stannous sulfate, stannous tartrate, chlorides, bromides, sulfates, nitrates, carboxylates or trifluoromethanesulfonates of rare earth metal elements, for example lanthanum, cerium, praseodymium, neodymium, samarium, europium, gadolinium, terbium, dysprosium, holmium, erbium, thulium, ytterbium and lutetium, cobalt chloride, ferrous chloride and yttrium chloride.

It will of course be appreciated that mixtures of a plurality of Lewis acids can be used.

It is also advantageous, where necessary, to stabilize the Lewis acid in aqueous solution by addition of an alkali metal chloride, for example lithium chloride or sodium chloride in particular. The lithium chloride or sodium chloride/Lewis acid molar ratio varies very widely, for example from 0 to 100, it being possible for the specific ratio to be adjusted depending on the stability of the Lewis acid in water.

Among the Lewis acids, zinc chloride, zinc bromide, zinc sulfate, zinc tetrafluoroborate, stannous chloride, stannous bromide, stannous chloride stabilized with lithium chloride, stannous chloride stabilized with sodium chloride and zinc chloride/stannous chloride mixtures, nickel chloride, nickel bromide, nickel acetylacetonate, and stannous trifluoromethanesulfonate are very particularly preferred.

The Lewis acid cocatalyst generally constitutes from 0.01 to 50 mol per mole of transition metal compound, more particularly of nickel compound, and preferably from 1 to 10 mol per mole.

The catalytic solution used for the hydrocyanation according to the invention may be prepared before its introduction into the reaction vessel, for example by addition of the appropriate amount of transition metal compound selected, of Lewis acid and possibly of reducing agent to the aqueous solution of the phosphine of formula (I). It is also possible to prepare the catalytic solution "in situ" simply by mixing these various constituents.

Although the reaction is typically carried out without a third solvent, it may be advantageous to add an inert, water-immiscible organic solvent, which may be that of the subsequent extraction.

Exemplary such solvents include aromatic, aliphatic or cycloaliphatic hydrocarbons which maintain the reaction medium in the two-phase state.

Thus, once the reaction is complete, it is very simple to separate out, on the one hand, an aqueous phase containing the sulfonated phosphine of formula (I), the transition metal compound and the Lewis acid and, on the other, an organic phase comprising the reactants employed in the reaction, the reaction products and, where appropriate, the water-immiscible organic solvent.

Exemplary organic solvents which may be used in the hydrocyanation process include benzene, toluene, xylenes, hexane and cyclohexane.

The process of the invention may be carried out continuously or discontinuously.

The hydrogen cyanide reactant may be prepared from metal cyanides, in particular sodium cyanide, or from cyanohydrins.

The hydrogen cyanide is introduced into the reactor in gaseous form or in liquid form. It may also be dissolved beforehand in an organic solvent.

When the subject process is carried out discontinuously, it is advantageous, in actual practice, to charge to a reactor which has been flushed beforehand using an inert gas (such as nitrogen or argon) either an aqueous solution containing all or certain of the various constituents, such as the sulfonated phosphine, the transition metal compound, the optional reducing agent and solvent, and the Lewis acid, or to charge said constituents thereto separately. Generally, the reactor is then heated to the desired temperature, followed by introduction of the pentenenitrile. Hydrogen cyanide is itself then introduced, preferably continuously and regularly.

When the reaction (whose progress may be monitored by assaying withdrawn samples) has ended, the reaction mixture is removed after cooling and the reaction products are isolated by separation of the phases after settling of the reaction medium, optionally followed by extraction of the aqueous layer using a suitable solvent, such as, for example, the aforesaid water-immiscible solvents.

The aqueous catalytic solution may then be recycled to a new hydrocyanation reaction.

When the process of the invention is carried out continuously, only the organic phase may be removed, while the aqueous catalytic phase remains in the reactor.

In order to further illustrate the present invention and the advantages thereof, the following specific examples are given, it being understood that same are intended only as illustrative and in nowise limitative.

EXAMPLE 1

(1) Preparation of the Ni/TSTPP Catalytic Solution

500 $cm^3$ of a solution of 300 mmol of the sodium salt of trisulfonated triphenylphosphine (TSTPP) in water were charged into a 1 liter glass round-bottomed flask fitted with a magnetic stirring bar and an ascending condenser; this solution was degassed. Next, with stirring and under a stream of argon, 20 g (73 mmol) of $Ni(cyclooctadiene)_2$ were introduced, followed by 350 $cm^3$ of previously degassed ortho-xylene.

The mixture was heated at 45° C. for 15 h. After cooling, the two-phase system separated out after settling had occurred and the strongly red-colored aqueous phase was withdrawn.

(2) Hydrocyanation of 3-Pentenenitrile 34.8 $cm^3$ of an aqueous solution of Ni/TSTPP catalyst, containing 5 mmol of Ni and 20 mmol of TSTPP, were charged into a 150 $cm^3$ glass reactor. The mixture was heated to 60° C. with stirring, and the following reagents were successively injected while maintaining this temperature:

(i) 3.2 $cm^3$ of an aqueous solution containing 20 mmol of zinc chloride, and (ii) 8 g (105 mmol) of 3-pentenenitrile (3PN).

Next, hydrogen cyanide was injected at a rate of 1.8 g/h (67 mmol/h) for 2 h.

At the end of the experiment, the reaction mixture obtained was cooled, the possible excess hydrogen cyanide injected was neutralized using concentrated sodium hydroxide solution and the various constituents were assayed by gas chromatography (GC).

The following results were obtained:

(a) Extent or degree of conversion (EC) of 3PN: 89%

(b) Yield (Yd) of adiponitrile (ADN) relative to the 3PN converted: 66%

(c) Yd of 2-methylglutaronitrile (MGN) relative to the 3PN converted: 26%

(d) Yd of 2-ethylsuccinonitrile (ESN) relative to the 3PN converted: 5%

(e) Yd of valeronitrile (VN) relative to the 3PN converted: 3%

(f) Linearity (*): 68%

(g) Activity of the catalyst (**): 20

(h) Production efficiency for ADN (relative to the volume of the aqueous phase): 90 g/h/l
   (*) ADN formed/ADN+MGN+ESN formed
   (**) number of moles of 3PN converted per mole of Ni employed

EXAMPLES 2 TO 5 AND COMPARATIVE EXAMPLE

The procedure of Example 1 was repeated employing the following charges and operating conditions:

(i) Ni: 5 mmol
(ii) TSTPP: 20 mmol
(iii) $ZnCl_2$: see Table 1
(iv) Water: qs 38 ml
(v) 3PN: 320 ml
(vi) HCN injection flow rate: 67 mmol/h
(vii) Temperature: 65° C.

The results obtained are reported in Table 1 (Yd of DN=yield of ADN+MGN+ESN relative to the 3PN converted):

TABLE 1

| Example | $ZnCl_2$ (in mmol) | Activity of the catalyst | % Yd of DN | Linearity |
|---|---|---|---|---|
| Example 2 | 1 | 5 | 88 | 73 |
| Example 3 | 5 | 14 | 97 | 74 |
| Example 4 | 20 | 30 | 97 | 63 |
| Example 5 | 40 | 30 | 97 | 57 |
| Comparative Example | 0 | 3 | 76 | 62 |

EXAMPLE 6

The procedure of Example 1 was repeated employing the following charges and operating conditions:

(i) Ni: 10 mmol
(ii) TSTPP: 20 mmol
(iii) $ZnCl_2$: 20 mmol
(iv) Water: qs 38 ml
(v) 3PN: 320 ml
(vi) HCN injection flow rate: 67 mmol/h
(vii) Temperature: 65° C.

The following results were obtained:

(a') Yd of DN: 98%
(b') Activity of the catalyst: 15
(c') Linearity: 71[{]jf44

EXAMPLES 7 AND 8

The procedure of Example 1 was repeated employing the following charges and operating conditions:

(i) Ni: 5 mmol
(ii) TSTPP: see Table 2
(iii) $ZnCl_2$: 20 mmol
(iv) Water: qs 38 ml
(v) 3PN: 320 ml
(vi) HCN injection flow rate: 67 mmol/h
(vii) Temperature: 65° C.

The results obtained are reported in Table 2:

TABLE 2

| Example | TSTPP (in mmol) | Activity of the catalyst | % Yd of DN | Linearity |
|---|---|---|---|---|
| Example 7 | 6 | 6 | 98 | 60 |
| Example 8 | 32 | 17 | 98 | 73 |

EXAMPLES 9 AND 10

The procedure of Example 1 was repeated employing the following charges and operating conditions:

(i) Ni: 5 mmol
(ii) TSTPP: 20 mmol
(iii) $ZnCl_2$: 20 mmol
(iv) Water: qs 38 ml
(v) 3PN: 320 ml
(vi) HCN injection flow rate: see Table 3
(vii) Temperature: see Table 3

The results obtained are reported in Table 3 (Example 4 is also reported in this Table):

TABLE 3

| Example | Temperature | HCN injection flow rate | Activity of the catalyst | % Yd of DN | Linearity |
|---|---|---|---|---|---|
| Example 9 | 45° C. | 17 mmol/h | 35 | 99 | 68 |
| Example 4 | 65° C. | 67 mmol/h | 30 | 97 | 63 |
| Example 10 | 85° C. | 135 mmol/h | 10 | 99 | 63 |

EXAMPLES 11 TO 23

The procedure of Example 1 was repeated employing the following charges and operating conditions:

(i) Ni: 5 mmol
(ii) TSTPP: 20 mmol
(iii) Lewis acid (nature of which indicated in Table 4): 20 mmol
(iv) Water: qs 35 ml
(v) 3PN: 200 mmol
(vi) HCN injection flow rate: 67 mmol/h
(vii) Temperature: 65° C.
(viii) Duration: 1 h The results obtained are reported in Table 4:

TABLE 4

| Example | Lewis Acid | Activity of the catalyst | Linearity |
|---|---|---|---|
| Example 11 | $MnBr_2$ | 8 | 64 |
| Example 12 | $MnCl_2$ | 8 | 66 |
| Example 13 | $FeCl_2$ | 6 | 68 |
| Example 14 | $CoCl_2/ZnCl_2$(*) | 19 | 72 |
| Example 15 | $ZnBr_2$ | 25 | 68 |
| Example 16 | $ZnI_2$ | 23 | 66 |
| Example 17 | $YCl_3$ | 8 | 75 |
| Example 18 | $CdBr_2$ | 20 | 69 |
| Example 19 | $SNBr_2$ | 10 | 88 |
| Example 20 | $SnCl_2$ | 12 | 88 |
| Example 21 | $SnCl_2/LiCl$(**) | 15 | 87 |

TABLE 4-continued

| Example | Lewis Acid | Activity of the catalyst | Linearity |
|---|---|---|---|
| Example 22 | $SnCl_2/ZnCl_2$(*) | 15 | 83 |
| Example 23 | $CeBr_3$ | 6 | 64 |

(*)equimolar mixture of 2 Lewis acids
(**)supplementary addition of 200 mmol of LiCl

EXAMPLES 24 TO 49

The procedure of Example 1 was repeated employing the following charges and operating conditions:

(i) Ni: 5 mmol
(ii) TSTPP: 20 mmol
(iii) Lewis acid (nature of which indicated in Table 5): 20 mmol
(iv) Water: qs 35 ml
(v) 3PN: 200 mmol
(vi) HCN injection flow rate: 67 mmol/h
(vii) Temperature: 65° C.
(viii) Duration: 1 h The results obtained are reported in Table 5:

TABLE 5

| Example | Lewis Acid | Activity of the catalyst | Linearity |
|---|---|---|---|
| Example 24 | $COCl_2$ | 3 | 84 |
| Example 25 | $CdCl_2$ | 5 | 72 |
| Example 26 | $SnSO_4$ | 5 | 89 |
| Example 27 | Tin tartrate | 4 | 87 |
| Example 28 | $LaCl_3$ | 3 | 70 |
| Example 29 | $CeCl_3$ | 3 | 73 |
| Example 30 | $PrCl_3$ | 4 | 75 |
| Example 31 | $NdCl_3$ | 4 | 75 |
| Example 32 | $SmCl_3$ | 3 | 77 |
| Example 33 | $EuCl_3$ | 5 | 87 |
| Example 34 | $GdCl_3$ | 3 | 78 |
| Example 35 | $DyCl_3$ | 4 | 78 |
| Example 36 | $HoCl_3$ | 3 | 81 |
| Example 37 | $ErCl_3$ | 3 | 80 |
| Example 38 | $TmCl_3$ | 6 | 77 |
| Example 39 | $YbCl_3$ | 4 | 81 |
| Example 40 | $LuCl_3$ | 4 | 81 |
| Example 41 | $NiBr_2$ | 2.2 | 83 |
| Example 42 | $Ni(acac)_2$(*) | 3.2 | 77 |
| Example 43 | $Mg(OTf)_2$(**) | 3.3 | 71 |
| Example 44 | $Zn(OTf)_2$(**) | 14 | 57 |
| Example 45 | $Sn(CF_3SO_3)_2$ | 3 | 87 |
| Example 46 | $NiCl_2$ | 2 | 91 |
| Example 47 | $La(CF_3SO_3)_3$ | 2 | 77 |
| Example 48 | $ZnSO_4$ | 7 | 77 |
| Example 49 | $Zn(BF4)_2$ | 11 | 77 |

(*)acac = acetylacetonate
(**)OTf = trifluoromethanesulfonate

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydrocyanation of an ethylenically unsaturated aliphatic mono-nitrile comprising contacting at least one such ethylenically unsaturated aliphatic mono-nitrile with hydrogen cyanide, in an aqueous reaction medium which comprises a catalytically effective amount of a three-component catalyst composition comprising (1) a transition metal; (2) a sulfonated phosphine said sulfonated phosphine having the general formula (I):

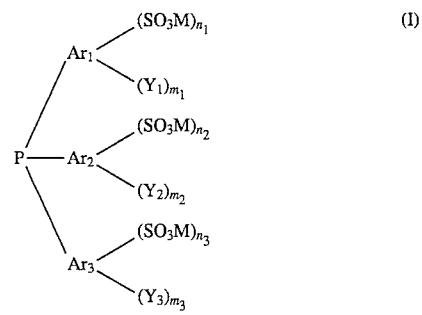

in which $Ar_1$, $Ar_2$ and $Ar_3$, which may be identical or different, are each aryl radicals; $Y_1$, $Y_2$ and $Y_3$, which may be identical or different, are each an alkyl radical having from 1 to 4 carbon atoms, an alkoxy radical having from 1 to 4 carbon atoms, a halogen atom, a CN group, an $NO_2$ group, an OH group, or a radial $NR_1R_2$ wherein $R_1$ and $R_2$, which may be identical or different, are each an alkyl radical having from 1 to 4 carbon atoms; M is an inorganic or organic cation selected such that the compound of formula (I) is water-soluble; $m_1$, $m_2$ and $m_3$ are integers, which may be identical or different, ranging from 0 to 5; and $n_1$, $n_2$ and $n_3$ are integers, which may be identical or different, ranging from 0 to 3, one or more of these being greater than or equal to 1; and (3) one or more Lewis acids, under reaction conditions to form a dinitrile through hydrocyanation of the ethylenically unsaturated aliphatic mono-nitrile, and forming a dinitrile through catalytic hydrocyanation of said ethylenically unsaturated aliphatic mono-nitrile.

2. The process as defined by claim 1, said ethylenically unsaturated aliphatic mono-nitrile comprising a linear pentenenitrile.

3. The process as defined by claim 2, said linear pentenenitrile comprising 3-pentenenitrile, 4-pentenenitrile, or mixture thereof.

4. The process as defined by claim 1, said transition metal compound being water-soluble, or dissolving in water under conditions of hydrocyanation.

5. The process as defined by claim 4, said transition metal compound comprising a compound of nickel, palladium, or iron.

6. The process as defined by claim 5, said transition metal compound comprising a nickel compound wherein the nickel is in the zero oxidation state.

7. The process as defined by claim 5, said transition metal compound comprising a nickel compound wherein the nickel is in an oxidation state greater than zero.

8. The process as defined by claim 7, the aqueous medium of reaction further comprising an organic or inorganic nickel-reducing agent.

9. The process as defined by claim 5, said transition metal compound comprising a nickel compound and said nickel compound being present in the aqueous medium of reaction in a concentration ranging from $10^{-4}$ to 1 mol of nickel per liter thereof.

10. The process as defined by claim 9, said nickel concentration ranging from 0.005 to 0.5 mol of nickel per liter of aqueous medium of reaction.

11. The process as defined by claim 1, said one or more Lewis acid cocatalyst(s) comprising an element selected from the group consisting of Groups Ib, IIb, IIIa, IIIb, IVa, IVb, Va, Vb, VIb, VIIb and VIII of the Periodic Table.

12. The process as defined by claim 11, said one or more Lewis acid cocatalyst(s) being stable and partially or completely soluble in the aqueous phase of the medium of hydrocyanation.

13. The process as defined by claim 12, said one or more Lewis acid cocatalyst(s) comprising a compound selected from the group consisting of halides, sulfates, nitrates, sulfonates, carboxylates, acetylacetonates, tetrafluoroborates and phosphates.

14. The process as defined by claim 13, said one or more Lewis acid cocatalyst(s) comprising a compound selected from the group consisting of zinc chloride, zinc bromide, zinc iodide, zinc trifluoromethanesulfonate, zinc acetate, zinc nitrate, zinc tetrafluoroborate, manganese chloride, manganese bromide, nickel chloride, nickel bromide, nickel cyanide, nickel acetylacetonate, cadmium chloride, cadmium bromide, stannous chloride, stannous bromide, stannous sulfate, stannous tartrate, a rare earth metal chloride, bromide, sulfate, nitrate, carboxylate or trifluoromethanesulfonate, cobalt chloride, ferrous chloride, yttrium chloride, and mixture thereof.

15. The process as defined by claim 1, the aqueous medium of reaction further comprising a Lewis acid-stabilizing amount of an alkali metal chloride.

16. The process as defined by claim 15, said alkali metal chloride stabilizer comprising lithium chloride or sodium chloride.

17. The process as defined by claim 16, wherein the lithium chloride or sodium chloride/Lewis acid molar ratio ranges up to 100.

18. The process as defined by claim 1, said one or more Lewis acid cocatalyst(s) being present in the aqueous medium of reaction in a concentration ranging from 0.01 to 50 mol thereof per mole of transition metal compound.

19. The process as defined by claim 18, said Lewis acid concentration ranging from 1 to 10 mol thereof per mole of transition metal compound.

20. The process as defined by claim 1, wherein said sulfonated phosphine having formula (I), M is $H^+$, an alkali or alkaline earth metal, a cation $N(R_3R_4R_5R_6)^+$ in which $R_3$, $R_4$, $R_5$ and $R_6$, which may be identical or different, are each an alkyl radical having from 1 to 4 carbon atoms or a hydrogen atom, or a metal cation, the benzenesulfonic acid salts of which being water-soluble.

21. The process as defined by claim 20, wherein said sulfonated phosphine having formula (I), $Ar_1$, $Ar_2$ and $Ar_3$ are phenyl radicals; $Y_1$, $Y_2$ and $Y_3$ are alkyl radicals having from 1 to 2 carbon atoms, or alkoxy radicals having from 1 to 2 carbon atoms; M is a cation selected from among $H^+$, cations of Na, K, Ca and Ba, $NH_4^+$, tetramethylammonium, tetraethyl-ammonium, tetrapropylammonium and tetrabutylammonium cations; $m_1$, $m_2$ and $m_3$ are integers ranging from 0 to 3; and $n_1$, $n_2$ and $n_3$ are integers ranging from 0 to 3, one or more of which being greater than 1.

22. The process as defined by claim 1, said sulfonated phosphine having formula (I) comprising a sodium, potassium, calcium, barium, ammonium, tetramethylammonium, or tetraethylammonium salt of mono(sulfophenyl)diphenylphosphine, di(sulfophenyl)phenylphosphine, or tri(sulfophenyl)phosphine.

23. The process as defined by claim 22, the $SO_3$ groups of the sulfonated phosphine being in the meta-position.

24. The process as defined by claim 1, said sulfonated phosphine being present in the aqueous medium of reaction in a concentration ranging from 0.5 to 2,000 mol thereof per mole of transition metal.

25. The process as defined by claim 24, said sulfonated phosphine concentration ranging from 2 to 300 mol thereof per mole of transition metal.

26. The process as defined by claim 1, carried out at a temperature ranging from 10° to 150° C.

27. The process as defined by claim 26, carried out at a temperature ranging from 30° to 120° C.

28. The process as defined by claim 1, comprising hydrocyanating a pentenenitrile into adiponitrile.

\* \* \* \* \*